US00PP36907P2

(12) United States Plant Patent
Kita et al.

(10) Patent No.: US PP36,907 P2
(45) Date of Patent: Sep. 2, 2025

(54) MANDARIN PLANT NAMED 'Mikanken4'

(50) Latin Name: ***Citrus* spp.**
Varietal Denomination: Mikanken4

(71) Applicant: EHIME PREFECTURE, Ehime (JP)

(72) Inventors: Keiji Kita, Ehime (JP); Haruhito Nakata, Ehime (JP); Yukinori Shigematsu, Ehime (JP); Yoji Hyodo, Ehime (JP); Hiroaki Mido, Ehime (JP); Takehiro Kikuchi, Ehime (JP); Yasuyuki Masamoto, Ehime (JP); Takae Sakimoto, Ehime (JP); Hiromichi Yakushiji, Ehime (JP); Takehiro Okusada, Ehime (JP); Taizo Ninomiya, Ehime (JP); Mitsutoshi Okamoto, Ehime (JP); Saki Yamamoto, Ehime (JP); Saki Miyoshi, Ehime (JP); Toya Hioki, Ehime (JP); Kei Kinoshita, Ehime (JP); Daijiro Sugawara, Ehime (JP)

(73) Assignee: EHIME PREFECTURE, Matsuyama (JP)

( * ) Notice: Subject to any disclaimer, the term of this patent is extended or adjusted under 35 U.S.C. 154(b) by 0 days.

(21) Appl. No.: 18/944,163

(22) Filed: Nov. 12, 2024

(51) Int. Cl.
*A01H 6/78* (2018.01)
*A01H 5/08* (2018.01)

(52) U.S. Cl.
USPC ..... Plt./202

(58) Field of Classification Search
USPC ..... Plt./156, 201, 202
See application file for complete search history.

(56) References Cited

U.S. PATENT DOCUMENTS

PP34,166 P3 * 4/2022 Smith ..... A01H 6/785 Plt./202
PP36,418 P2 * 2/2025 Nakata ..... A01H 6/785 Plt./202

* cited by examiner

*Primary Examiner* — Karen M Redden
(74) *Attorney, Agent, or Firm* — Seckel IP, PLLC

(57) ABSTRACT

A new variety of citrus 'Mikanken4' that has dark orange fruit color, without seeds, high juiciness, orange-like flavor, ease of peeling the fruit by hand, good appearance, and good tasting qualities.

3 Drawing Sheets

Common name: Mandarin.
Botanical classification: *Citrus* spp.
Variety denomination: 'Mikanken4'.

BACKGROUND OF THE NEW VARIETY

The present invention relates to a new and distinct variety of Mandarin, *Citrus* L., which has been given the variety denomination 'Mikanken4'.

ORIGIN OF THE VARIETY

The parent varieties are 'Kiyomi' (female parent) (not patented in the U.S.) and MINEOLA' (male parent) (not patented in the U.S.), respectively.

The variety was developed and propagated in Uwajima, Ehime, Japan.

The variety was reproduced asexually by vegetative reproduction by top grafting one-year-old scions on rootstocks in Uwajima, Ehime, Japan. The rootstock variety was 'MIYAGAWAWASE' (not patented in the U.S.)

In 1989, the parent varieties were crossed.

In 1990, collected seeds were grown.

In 1992, saplings were grafted on top of rootstock 'MIYAGAWAWASE' (not patented in the U.S.)

In 1995, the first fruit was harvested, and lines were primary selected.

In 1997, plants were secondary selected, and the variety was named 'Mikanken4'.

In 2024, breeding was completed with determination of distinct, uniform, and stable (DUS) status confirmed, and the variety was named 'Mikanken 4'.

Cultivation of the variety does not require special conditions or treatments.

The variety is currently mainly intended for fruit production.

SUMMARY OF THE VARIETY

The new mandarin plant 'Mikanken4' has leaf blades with very small length/width ratio, fruit with dark orange surface color, and late maturity for consumption (typically May), which distinguish 'Mikanken4' from its female parent 'Kiyomi'.

Further, the new mandarin plant 'Mikanken4' has fruit with an absence of neck, which distinguishes it notably from its male parent 'MINEOLA'.

Also, the new mandarin plant 'Mikanken4' having leaf blades with very small length/width ratio, and late maturity for consumption (typically May), and its fruit having a proximal part with a flattened general shape, distinguish it notably from the comparative variety 'Ehimekashi48', A comparison with the female parent 'KIYOMI' is as follows (evaluation based on averages):

TABLE 1

| No. | Characteristics | Female parent 'KIYOMI' | Present variety 'Mikanken4' |
|---|---|---|---|
| 16 | Leaf blade: ratio length/width | Small (2.2) | Very small (1.9) |
| 83 | Fruit surface: predominant color(s) | Yellow orange RHS 17A | Orange RHS N25C |
| 119 | Time of maturity of fruit for consumption | Medium (March) | Late (May) |

A comparison with the male parent 'MINEOLA' is as follows (evaluation based on averages):

TABLE 2

| No. | Characteristics | Male parent 'MINEOLA' | Present variety 'Mikanken4' |
|---|---|---|---|
| 66 | Fruit: presence of neck | Present | Absent |

A comparison with the reference variety 'Ehimekashi48' is as follows (evaluation based on averages):

TABLE 3

| No. | Characteristics | Reference variety 'Ehimekashi48' | Present variety 'Mikanken4' |
|---|---|---|---|
| 16 | Leaf blade: ratio length/width | Small (2.2) | Very small (1.9) |
| 65 | Fruit: general shape of proximal part | Strongly rounded | Flattened |
| 119 | Time of maturity of fruit for consumption | Medium (March) | Late (May) |

BRIEF DESCRIPTION OF THE DRAWINGS

In the accompanying drawings, which are as nearly true as is reasonable possible to make in a color illustration of this type.

Figure 1:
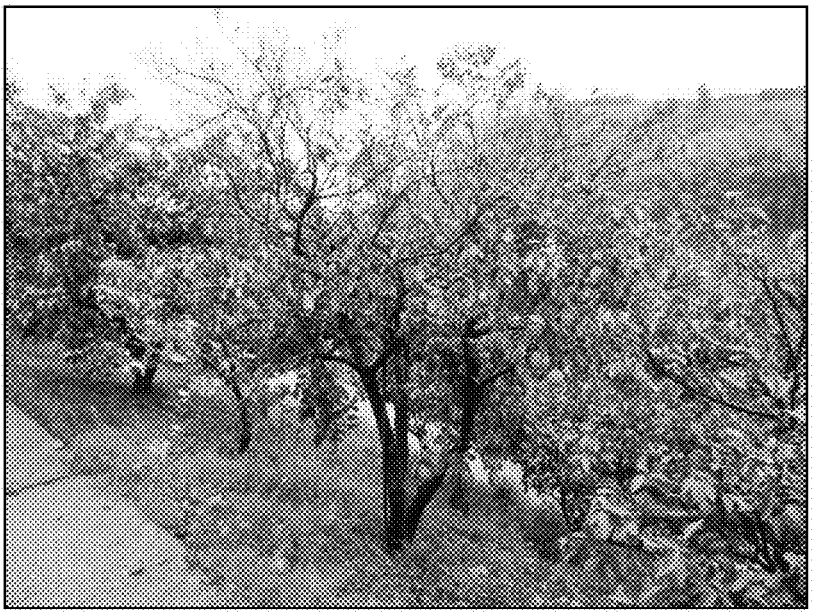
FIG. 1 is a color photograph showing a general view of the mandarin plant 'Mikanken4' bearing fruits.
Figure 2:
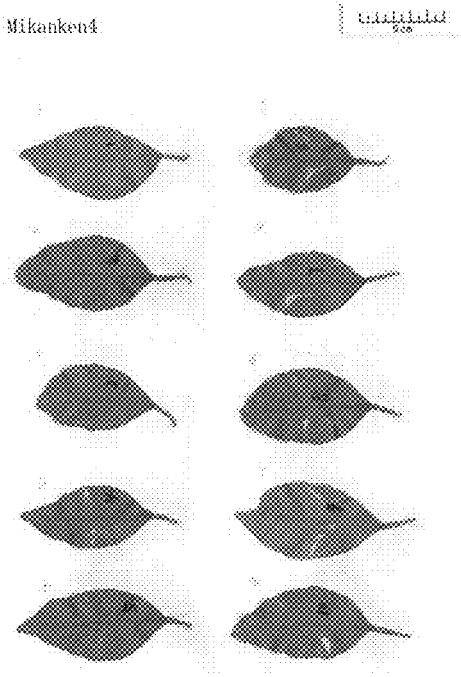
FIG. 2 is a color photograph showing leaves of 'Mikanken4'
Figure 3:
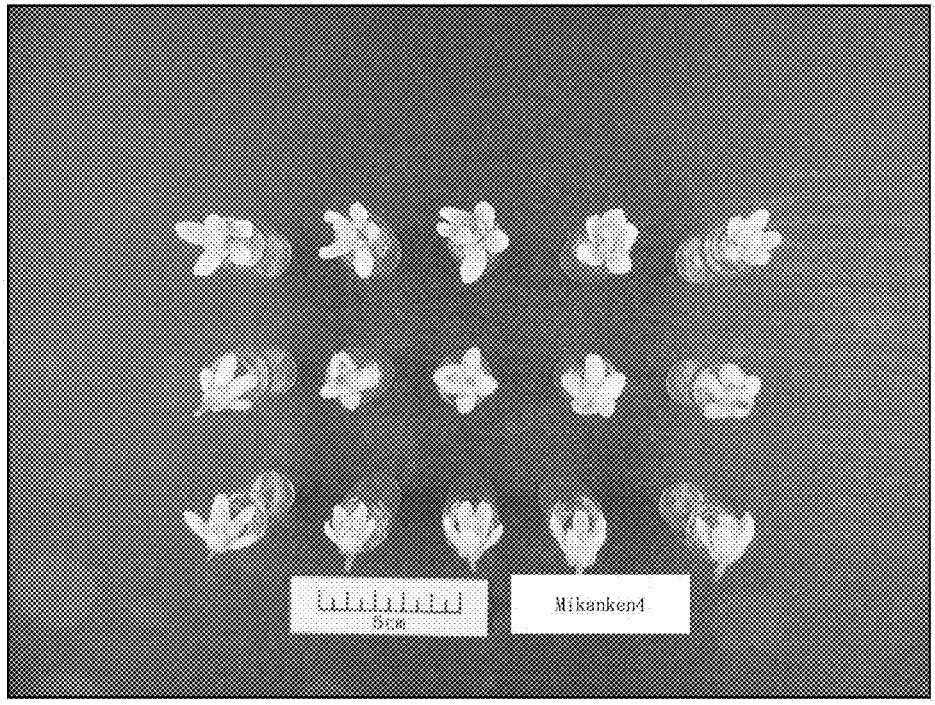
FIG. 3 is a color photograph showing flowers of 'Mikanken4'.
Figure 4:
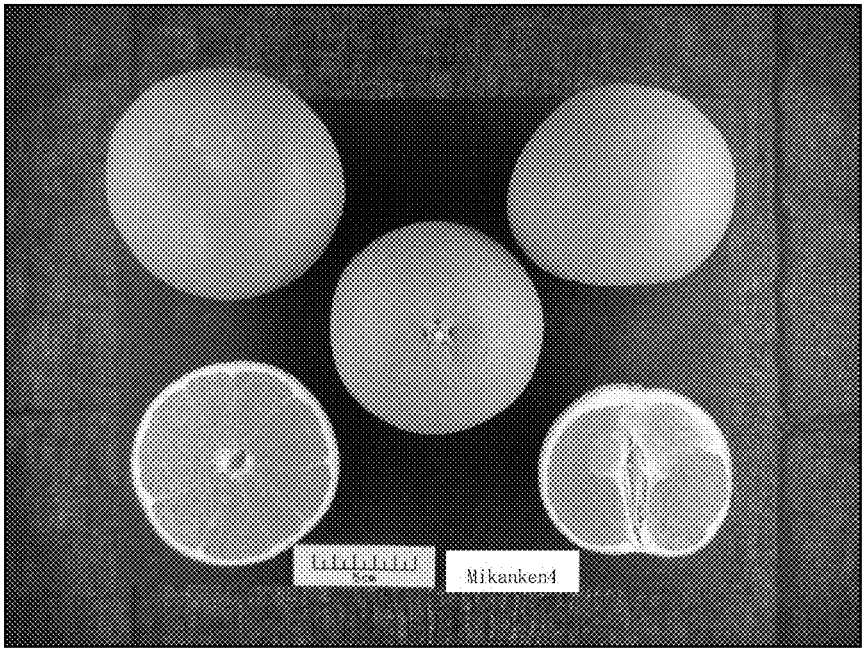
FIG. 4 is a color photograph showing fruits of 'Mikanken4'.
Figure 5:
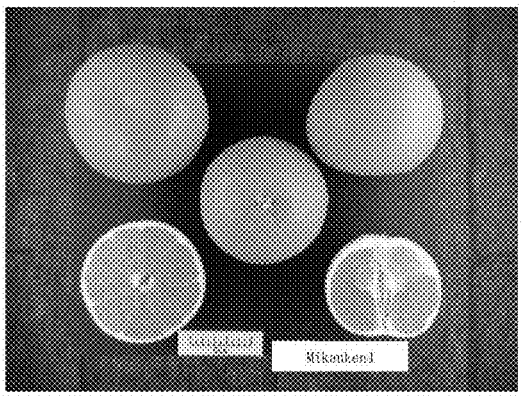
FIG. 5 is a color photograph showing the leaves of 'Mikanken4' and its female parent 'KIYOMI', illustrating the difference in the predominant color of fruit surface.
Figure 5:
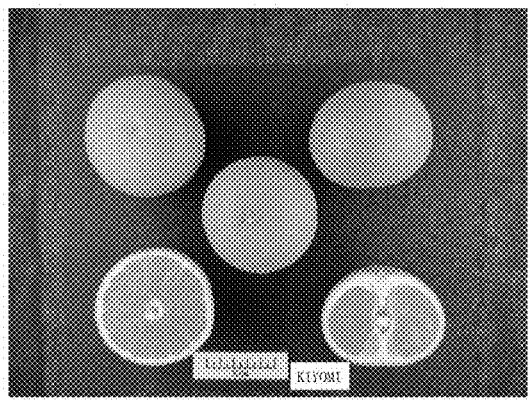
Figure 6:
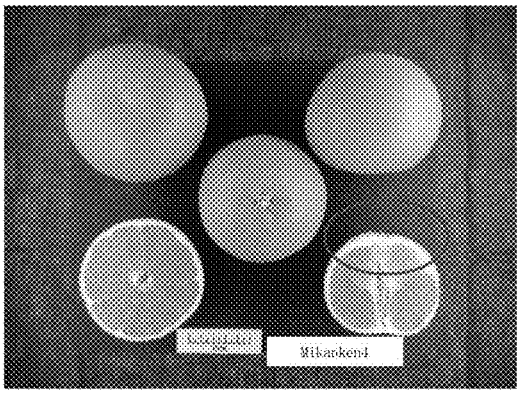
FIG. 6 is a color photograph showing fruits of 'Mikanken4' and the comparative variety 'Ehimekashi48', illustrating the difference in the general shape of the proximal part.
Figure 6:
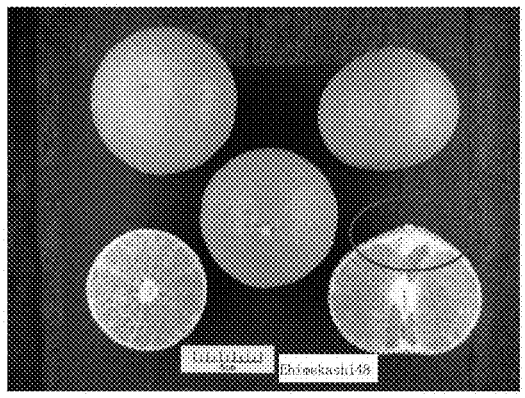

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'Mikanken4' plants evaluated in 2024 (including for the comparison with the reference plants 'KIYOMI' and 'Ehimekashi48'). Values as provided are averages.

The plants shown on the photographs were grown at Uwajima, Ehime, Japan. The plant is a 15-year grown after top grafting. The tree was photographed on Mar. 25, 2024, the flowers were photographed on Apr. 25, 2024, the mature leaves were photographed on Mar. 25, 2024, and the fruit were photographed on Mar. 29, 2024.

Colors are given according to the RHS (Royal Horticultural Society) Colour Chart (Fourth Ed., 2001).

BOTANICAL DESCRIPTION

TABLE 4

| No. | Characteristics | States | Values |
|---|---|---|---|
| 1. | Ploidy | Diploid | |
| 2. | Tree: growth habit | Spreading | |
| 3. | Tree: density of spines | Intermediate | |
| 4. | Tree: length of spines | Short | 2.2 cm |
| 5. | Tree height | | 2.7 m |
| 6. | Tree spread | | 3.2 m |
| 7. | Trunk diameter | | 27.7 cm |
| 8. | Trunk texture | Rough | |
| 9. | Trunk color | Green brown | RHS 152B |
| 10. | Crotch angle | | 47.5° |
| 11. | Branch length | Short | 9.8 cm |
| 12. | Branch texture | Smooth | |
| 13. | Branch color | Brown green | RHS 146A |
| 14. | Leaf blade: length (apical leaflet in case of compound leaf) | Medium | 8.0 cm |
| 15. | Leaf blade: width (as for 5) | Medium | 4.3 cm |
| 16. | Leaf blade: ratio length/width (as for 5) | Very small | 1.9 |
| 17. | Leaf blade: shape in cross section (as for 5) | Intermediate | |
| 18. | Leaf blade: twisting | Absent or weak | |
| 19. | Leaf blade: blistering | Absent or weak | |
| 20. | Leaf blade: green color | Medium | |
| 21. | Leaf blade: undulation of margin | Intermediate | |
| 22. | Leaf blade: incisions of margin | Absent | |
| 23. | Leaf blade: shape of apex | Acute | |
| 24. | Leaf blade: emargination at tip | Present | |
| 25. | Leaf blade size | Medium | 22.4 $cm^2$ (length 8.0 cm, width 4.3 cm) |
| 26. | Leaf arrangement | Alternate | |
| 27. | Leaf type | Simple leaf | |
| 28. | Leaf shape | Fusiform | |
| 29. | Leaf color: upper surface | Dark green | RHS 141A |
| 30. | Leaf color: lower surface | Brown green | RHS 137D |
| 31. | Petiole: length | Medium | 1.8 cm |
| 32. | Petiole: presence of wings | Present | |
| 33. | Petiole diameter | Medium | 1.8 mm |
| 34. | Petiole color | Dark green | RHS 141A |
| 35. | Petiole wings | Present | |
| 36. | Petiole attachment | | (Not examined) |
| 37. | Petiole texture | Smooth | |
| 38. | Varieties with petiole wings present only: Petiole: width of wings | Narrow | 3.3 mm |
| 39. | Flower: type | Single | |
| 40. | Flower: diameter of calyx | — | 0.9 cm |
| 41. | Flower: number of petals | | 5 |
| 42. | Flower: sepal size | | length 0.55 cm, width 0.93 cm |
| 43. | Flower: sepal shape | Synsepalous calyx | |
| 44. | Flower: sepal color | Light green | RHS 144D |
| 45. | Flower: length of petal | Short | 13.7 mm |
| 46. | Flower: width of petal | Medium | 6.0 mm |
| 47. | Flower: ratio length/ width of petal | — | 2.3 |
| 48. | Petal color: upper surface | White | RHS 155A |

TABLE 4-continued

| No. Characteristics | States | Values |
|---|---|---|
| 49. Petal color: lower surface | White | RHS 155A |
| 50. Petal texture | Smooth | |
| 51. Flower: length of stamens | — | 9.2 mm |
| 52. Flower: blooming period | Medium | May 1-10 |
| 53. Flower: fragrance | Present | |
| 54. Flower: fertility | Present | |
| 55. Pollen abundance | Absent | |
| 56. Pollen color | | (Not examined) |
| 57. Anther: color | Light yellow | RHS 8D |
| 58. Style: length | — | 6.7 mm |
| 59. Infructescence: clustering of fruits | Present | |
| 60. Fruit: length | — | 7.4 cm |
| 61. Fruit: diameter | — | 8.6 cm |
| 62. Fruit: ratio length/diameter | Medium | 1.16 |
| 63. Fruit: position of broadest part | At middle | |
| 64. Fruit: shape in transverse section | Circular | |
| 65. Fruit: general shape of proximal part (excluding neck, collar and depression at stalk end) | Flattened | |
| 66. Fruit: presence of neck | Absent | |
| 67. Fruit: presence of depression at stalk end | Present | |
| 68. Fruit: depth of depression at stalk end | — | 2.0 mm |
| 69. Fruit: presence of constriction at stalk end | Absent | |
| 70. Fruit: number of radial grooves at stalk end | Intermediate | |
| 71. Fruit: length of radial grooves at stalk end | Short to medium | 10.1 |
| 72. Fruit: presence of collar | Absent | |
| 73. Fruit: abscission layer between floral disc and fruit | Absent or weakly developed | |
| 74. Fruit: general shape of distal part (excluding nipple, bulging of navel and depression at distal end) | Flattened | |
| 75. Fruit: presence of depression at distal end | Present | |
| 76. Fruit: depth of depression at distal end | — | 2.6 mm |
| 77. Fruit: diameter of depression at distal end | — | 14.5 mm |
| 78. Fruit: presence of areola | Absent | |
| 79. Fruit: diameter of stylar scar | — | 2.1 mm |
| 80. Fruit: persistence of style | None | |
| 81. Fruit: presence of navel opening | Absent | |
| 82. Fruit: presence of radial grooves at distal end | Absent | |
| 83. Fruit surface: predominant color(s) | Orange | RHS N25C |
| 84. Fruit surface: glossiness | Medium | |
| 85. Fruit surface: roughness | Smooth | |
| 86. Fruit surface: size of oil glands | All more or less the same size | |
| 87. Fruit surface: size of larger oil glands | Small | |
| 88. Fruit surface: conspicuousness of larger oil glands | Strong | |
| 89. Fruit surface: presence of pitting and pebbling on oil glands | Pitting and pebbling absent | |
| 90. Fruit rind: thickness | Medium | 3.5 mm |

TABLE 4-continued

| No. Characteristics | States | Values |
|---|---|---|
| 91. Fruit weight | Heavy | 286 g |
| 92. Fruit rind: adherence to flesh | Weak | |
| 93. Fruit rind: strength | Weak | |
| 94. Fruit rind: oiliness | Dry | |
| 95. Fruit rind: conspicuousness of oil glands on inner surface | Absent or weakly conspicuous | |
| 96. Fruit: color of albedo | Light yellow | RHS 8C |
| 97. Fruit: density of albedo | Medium | |
| 98. Fruit: amount of albedo adhering to flesh (strands excluded) | Small | |
| 99. Fruit: presence of albedo strands | Absent | |
| 100. Fruit: main color of flesh | Dark orange | RHS N25C |
| 101. Fruit: filling of core | Absent or very sparse | |
| 102. Fruit: diameter of core | Very small | 10.9 mm |
| 103. Fruit: presence of rudimentary segments | Absent or very weak | |
| 104. Fruit: number of well-developed segments | — | 12 |
| 105. Fruit: coherence of adjacent segment walls | Strong | |
| 106. Fruit: strength of segment walls | Weak | |
| 107. Fruit: length of juice vesicle | — | 6.2 mm |
| 108. Fruit: thickness of juice vesicles | — | 2.6 mm |
| 109. Fruit; conspicuousness of juice vesicle walls | High | |
| 110. Fruit: coherence of juice vesicles | Medium | |
| 111. Fruit: presence of navel (viewed internally) | Absent or very rare | |
| 112. Fruit: juiciness | High | |
| 113. Fruit juice: total soluble solids | High | 12.8 (Brix) |
| 114. Fruit juice: acidity | High | 1.95 mg/100 ml |
| 115. Fruit: strength of fiber | Weak | |
| 116. Fruit: number of seeds (controlled manual self-pollination) | Absent or very few | 0 |
| 117. Fruit: number of seeds (open pollination) | Absent or very few | 0 |
| 118. Seed: polyembryony | Absent | |
| 119. Time of maturity of fruit for consumption | Late | May |
| 120. Productivity (pounds or bushels per acre) | | (Not examined) |
| 121. Fruit: parthenocarpy | Present | |

Other features of the plant are as follows:

Disease and Pest resistance: Normal resistance was observed for pests and diseases in Uwajima, Ehime, Japan.

Tree hardiness: USDA Hardiness Zone Pa-9b.

Fruit ship ability: medium, slightly inferior compared to the variety 'IYOKAN' which has excellent storage ability.

Fruit storage ability: medium.

The invention claimed is:

1. A new and distinct variety of citrus named 'Mikanken4', substantially as described and illustrated herein.

* * * * *